United States Patent [19]
Cooper

[11] Patent Number: 5,222,964
[45] Date of Patent: Jun. 29, 1993

[54] INTRALUMINAL STENT

[76] Inventor: William I. Cooper, 300 N. Fourteenth St., Easton, Pa. 18042

[21] Appl. No.: 845,021

[22] Filed: Mar. 3, 1992

[51] Int. Cl.⁵ ............................................. A61B 17/00
[52] U.S. Cl. ................................. 606/156; 606/155; 128/831; 128/887
[58] Field of Search ................. 606/152-156, 606/148; 128/772, 831, 830, 843, 887, 889; 604/901

[56] References Cited

U.S. PATENT DOCUMENTS

| | | | |
|---|---|---|---|
| 3,683,926 | 8/1972 | Suzuki | 606/155 |
| 3,993,078 | 11/1976 | Bergentz | 606/156 |
| 4,595,000 | 6/1986 | Hamou | 128/831 |
| 4,674,506 | 6/1987 | Alcond | 606/153 |
| 4,721,109 | 1/1988 | Healey | 606/156 |
| 4,920,962 | 5/1990 | Proulx | 606/152 |
| 5,037,428 | 8/1991 | Picha et al. | 606/155 |

Primary Examiner—Stephen C. Pellegrino
Assistant Examiner—Gary Jackson
Attorney, Agent, or Firm—Pollock, Vande Sande & Priddy

[57] ABSTRACT

A tapered stent made of resilient material for interconnecting portions of a Fallopian tube after a resection procedure. The stent is tapered to conform to the tapered inner surface of the Fallopian tube and is provided with at least one suture on at least one end for use in inserting the stent within the Fallopian tube and to secure the stent in place.

8 Claims, 1 Drawing Sheet

INTRALUMINAL STENT

The present invention relates to a method and means for surgically interconnecting portions of a Fallopian tube after a resection procedure.

BACKGROUND OF THE INVENTION

Surgical procedures which involve interconnecting tubular body members such as blood vessels, typically involve securing two ends together by sutures. However, this technique has the disadvantages that it must be carried out by a highly-skilled surgeon and it is time-consuming.

In view of the problems involved in directly suturing together two cut ends of a blood vessel, techniques have been developed using a tubular member, or stent, as a sleeve which is inserted within the end portions of the blood vessel to be united. The stent may then be sutured to the walls of the end portions being reconnected. See, for example, U.S. Pat. No. 3,993,078 to Bergentz et al for a description of an insert for use in vascular surgery. See also U.S. Pat. No. 4,190,989 to Ablaza for a description of a tubular graft for repair of arteries.

While the use of an insert in surgical procedures is widespread, Fallopian tubal reanastomosis is presently performed only through microsurgical techniques carried out through a major incision in the abdominal wall. An ideal reanastomotic technique for joining end portions of a resected Fallopian tube would permit a laparoscopic approach, thereby avoiding a major incision. However, the few attempts which have been reported in the literature of joining resected Fallopian tube end portions using a laparoscopic approach have all met with failure. It would be a significant advance in the art to provide a procedure and means for interconnecting the end portions of a resected Fallopian tube using a laparoscopic approach.

SUMMARY OF THE INVENTION

In accordance with the present invention there is provided an intraluminal stent adapted for Fallopian tube reanastomosis and a method of rejoining the end portions of a resected Fallopian tube using such a stent.

The stent comprises a solid elongated element having an outer surface uniformly tapered throughout its length to conform to the tapered inner surface of the walls of the Fallopian tube at the juncture of the two end portions which were formed in a resection procedure. In a preferred embodiment, at least one suture is provided at the proximal (small end) portion of the stent, and in a most preferred embodiment, at least one suture is provided at each end portion of the stent.

In carrying out the method of the present invention, the tapered stent is passed into the fimbriated end of a resected Fallopian tube, small end first, and then past the resected ends and into the proximal portion of the tube. The end portions of the Fallopian tube are brought together and sutured in place.

Since the stent is tapered it can fit snugly into both the distal and proximal portions of the Fallopian tube, mimicking the normal diameters (increasing distally) of the Fallopian tube. This produces a wedging effect on the tissues which will help prevent the reanastomosis site from contracting into a smaller lumen than the remainder of the tube. Because the stent will be left in for a few days during the healing process, and removed in a later laparoscopy, the healing process will continue past the development of scar tissue so that, when the stent is removed, the lumen will remain relatively scar-free and of normal diameter.

An additional advantage, of course, is the fact that this method can be used with a laparoscope, thus avoiding a major incision.

DETAILED DESCRIPTION OF THE INVENTION

The stent is formed of a soft biologically inactive material such as, for example, soft sponge rubber or a soft plastic with enough flexibility and resilience to avoid compression damage to the lumen of the tube, and to permit passage through the flexible Fallopian tube without damaging it or turning upon itself within the lumen during insertion. The stent is tapered to closely conform to the tapered shape of the Fallopian tube. If the stent is viewed in cross-section as in FIG. 2, the angle between converging lines 16 and 17 is preferably in the range from about 2° to about 6°. The stent should be sufficiently long so that it serves its function of connecting the two resected portions of the Fallopian tube together and in a preferred embodiment, the stent has a length from about 2 cm to about 4 cm with a length of about 3 cm being preferred. The diameter at the small end of the stent may suitably range from about 1 mm to about 3 mm, and the diameter at the large end will typically be about 4 mm.

In a preferred embodiment, the stent is provided with at least one fine suture, for example, a size 6-0 suture, at the small end which serves the dual function of (1) helping to insert the stent into the Fallopian tube, and (2) helping secure the stent in place, as is discussed below. The length of each suture is not critical, but is preferably at least about 10 cm long. This suture is preferably provided with its own standard atraumatic needle.

In a preferred embodiment of the stent, at least one larger suture is provided at its large end. This suture need not be equipped with a needle since its primary function is to serve as a point of contact to pull the stent from the Fallopian tube when it is to be removed. The length of this suture is not critical and a length of about 10 cm or more is preferred.

Figure 1:
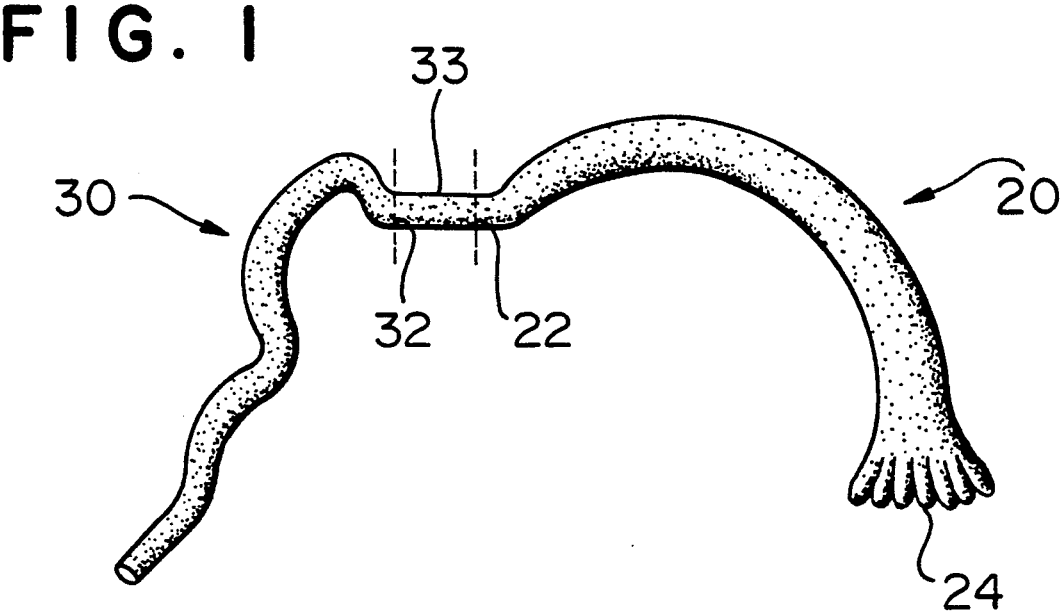
FIG. 1 is an illustration of a Fallopian tube identifying a typical portion to be resected.

Referring to the drawings, FIG. 1 illustrates a Fallopian tube which is to be resected by removing portion 33, thus forming a distal portion 20 having a fimbriated end 24 and a cut end 22 and a proximal portion 30 having a cut end 32.

Figure 2:
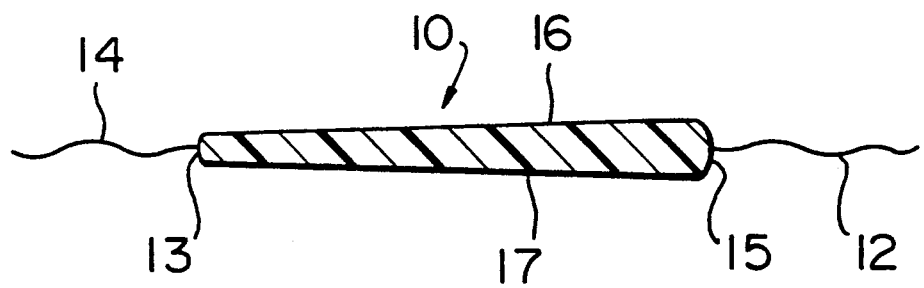
FIG. 2 is a cross-sectional view of a tapered stent and its attached sutures.

FIG. 2 is a cross-section of a tapered stent 10 having a suture 12 at large diameter end 15 and a suture 14 at small diameter end 13.

Figure 3:
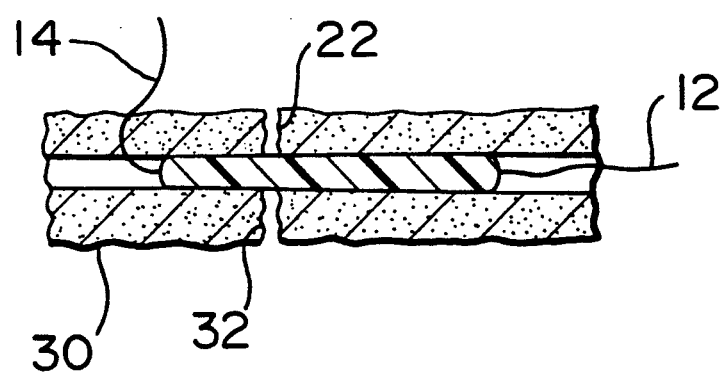
FIG. 3 is a sectional view of a stent joining together portions of a Fallopian tube after resection in accordance with the present invention.

FIG. 3 illustrates the stent in place for securing the resected ends 22, 32 together. In a preferred method of inserting the stent into the position shown in FIG. 3, a probe, such as a lacrimal duct probe is inserted into the small end 22 of distal portion 20 and out through fimbriated end 24 where it is secured to suture 14. The probe is retracted through distal portion 20, pulling stent 10 past the resected end 22. The probe is removed from suture 14. The needle is passed into the lumen of the proximal portion 30 and through its wall. The suture 14 is pulled to urge the stent against the lumen walls and bring the two ends 22, 32 together as shown in FIG. 3. The suture is then anchored to the uterus or a convenient ligament to hold the stent securely wedged in place, and the needle is removed from the suture. After the two portions of the Fallopian tube are healed, a second laparoscopy is performed and the stent is removed after cutting the anchoring suture.

What is claimed is:

1. A method of joining together resected end portions of a Fallopian tube which has been resected resulting in a first distal portion having a cut end portion and a fimbriated end portion and a second proximal portion having a cut end portion, said method comprising:
   a) providing a stent having a diameter substantially equal to the inner diameter of a Fallopian tube, and having first and second end portions and at least one suture means secured to each of said end portions;
   b) inserting the suture means which is secured to said first end portion of said stent into said first distal portion of said Fallopian tube through said fimbriated end portion, past said cut end portion of said first distal portion and said second proximal portion, and through a wall of said cut end portion of said second proximal portion;
   c) pulling on said suture means which is secured to said first end portion of said stent to pull said stent into contact with said resected end portions, and bringing said resected end portions into contact with each other; and,
   d) securing said stent in place at said resected end portions by means of said suture.

2. An intraluminal stent for use in carrying out a surgical procedure for joining together first and second ends of a tapered portion of a resected Fallopian tube, said stent comprising an elongated solid member formed of a biologically compatible, resilient material, said stent being uniformly tapered throughout its length for substantially conforming throughout its length to the taper of said Fallopian tube.

3. A stent according to claim 2 having a taper of from about 2° to about 6°.

4. A stent according to claim 2 having a length from about 2 centimeters to about 4 centimeters.

5. A stent according to claim 2 formed of sponge rubber.

6. A stent according to claim 2 formed of a soft plastic.

7. A stent according to claim 2 provided with at least one suture secured to at least one end portion of said stent.

8. A stent according to claim 7 wherein said suture has a length of at least about 10 centimeters.

* * * * *